US00PP28260P3

(12) United States Plant Patent
Layt

(10) Patent No.: US PP28,260 P3
(45) Date of Patent: Aug. 8, 2017

(54) ***LOMANDRA* PLANT NAMED 'LM600'**

(50) Latin Name: ***Lomandra* hybrid**
Varietal Denomination: LM600

(71) Applicant: Todd Anthony Layt, Clarendon (AU)

(72) Inventor: Todd Anthony Layt, Clarendon (AU)

( * ) Notice: Subject to any disclaimer, the term of this patent is extended or adjusted under 35 U.S.C. 154(b) by 62 days.

(21) Appl. No.: 14/756,774

(22) Filed: Oct. 9, 2015

(65) Prior Publication Data

US 2016/0113182 P1 Apr. 21, 2016

(30) Foreign Application Priority Data

Oct. 16, 2014 (AU) ..... PBR 2014248

(51) Int. Cl.
*A01H 5/12* (2006.01)

(52) U.S. Cl.
USPC ..... Plt./373

(58) Field of Classification Search
USPC ..... Plt./373, 263.1, 384
See application file for complete search history.

*Primary Examiner* — June Hwu
(74) *Attorney, Agent, or Firm* — Samuel R. McCoy, Jr.

(57) ABSTRACT

'LM600' is a distinctive cultivar of *Lomandra* Labill. which is characterized by the combination of a short plant height, a weeping growth habit and fine-textured, dark green foliage. The new variety propagates successfully by division and tissue culture and has shown to be uniform and stable in the resulting generations from asexual propagation.

1 Drawing Sheet

Latin name of the genus and species:

The Latin name of the genus and species of the novel variety disclosed herein is *Lomandra* hybrid.

Variety denomination: The inventive variety of *Lomandra* Labill. disclosed herein has been given the variety denomination 'LM600'.

CROSS REFERENCE TO RELATED APPLICATIONS

This application claims priority to the Australian Plant Breeders Rights application number 2014/248, filed on Oct. 16, 2014, which is herein incorporated by reference.

BACKGROUND OF THE INVENTION

The present invention relates to a new and distinct perennial variety of *Lomandra* Labill., which has been given the variety denomination of 'LM600'. Its market class is PLT/373. 'LM600' is intended for use in landscaping and as a decorative plant.

Parentage: 'LM600' is a seedling selection resulting from an open-pollination and seedling selection process carried out by the inventor at his commercial breeding facility in Clarendon, NSW, Australia. In early spring of 2010, a fine-leafed female *Lomandra* Labill. breeding line, developed by the same inventor, was grown in close proximity to other male breeding lines developed by the inventor and also with the commercial cultivar *Lomandra longifolia* 'LM300' (U.S. Plant Pat. No. 15,420). These plants were allowed to openly pollinate. In early summer of 2010, seed was collected from the female breeding line. In spring of 2011, said seed was germinated and, of the progeny, seven seedlings that exhibited fine-textured foliage were isolated for further observation. Later in 2011, one of these plants was selected for its compact size and fine foliage when compared to the female parent and other progeny. This new and distinctive cultivar was given the name 'LM600'.

Asexual Reproduction: 'LM600' was first asexually propagated in early 2012 by division of the plant's crown in Clarendon, NSW, Australia and has since been asexually reproduced by meristematic tissue culture propagation. The distinctive characteristics of the inventive 'LM600' variety have proven to be stable through five generations and clones so produced maintain the distinguishing characteristics of the original plant.

SUMMARY OF THE INVENTION

The following traits have been repeatedly observed and represent the characteristics of the new cultivar. These characteristics, in combination, distinguish 'LM600' as a distinct cultivar of *Lomandra* Labill.:

1. 'LM600' exhibits a short plant height; and
2. 'LM600' exhibits a weeping growth habit; and
3. 'LM600' exhibits fine-textured foliage; and
4. 'LM600' exhibits dark green foliage.

BRIEF DESCRIPTION OF THE FIGURES

The FIGURE illustrates, as true as is reasonably possible to obtain in color photographs of this type, an exemplary 'LM600' specimen of approximately 12 months of age in a 400 mm (approximate) nursery pot, grown at a commercial plant breeding facility in Clarendon, NSW, Australia.

BOTANICAL DESCRIPTION OF THE PLANT

The following is a detailed botanical description of a new and distinct variety of a *Lomandra* ornamental plant known as 'LM600'. Plant observations were made on plants grown in Clarendon, NSW, Australia. Unless indicated otherwise, the descriptions disclosed herein are based upon observations made in September 2015 of 30 month old 'LM600' plants grown outdoors from rooted cuttings in 250 mm nursery pots filled with soilless potting media, maintained with granular slow release fertilizer and regularly watered with overhead irrigation. No pest and disease measures were taken.

Those skilled in the art will appreciate that certain characteristics will vary with older or, conversely, younger plants. 'LM600' has not been observed under all possible environmental conditions. Where dimensions, sizes, colors and other characteristics are given, it is to be understood that such characteristics are approximations or averages set forth as accurately as practicable. The phenotype of the variety may vary with variations in the environment such as season, temperature, light intensity, day length, cultural conditions and the like. Color notations are based on *The Royal Horticultural Society Colour Chart*, The Royal Horticultural Society, London, 2001 edition. Note that generic color descriptions such as 'green' do not exist in the R.H.S. charts and the corresponding R.H.S. colors are quoted.

A botanical description of 'LM600' and comparisons with the seed parent and several similar varieties of common knowledge are provided below.

General plant description:

*Plant habit*.—Grass-like perennial with arched foliage; rhizomatous plant forming a dense tussock.

*Reproduction*.—Dioecious; male of the species.

*Height*.—25 cm as measured.

*Width*.—80 cm as measured.

*Bloom period*.—Spring.

*Hardiness*.—USDA Zone 8 to 11.

*Propagation*.—Propagation is accomplished by dividing the crown of the plant and also by way of meristematic tissue culture propagation.

*Crop time*.—Time to develop a rooted cutting is approximately 8 weeks, from division. An average crop time is approximately 6 to 9 months to produce a mature and marketable 1-gallon nursery container, beginning with a rooted cutting.

*Environmental tolerances*.—Shade and drought tolerant.

*Pest and disease susceptibility or resistance*.—In common with the species, none of note.

Roots: Similar to other *Lomandra*, 'LM600' has a large root structure; roots are fibrous and spreading.

Rhizomes: Short (1.5 cm to 3 cm); rhizome color with the leaf sheath removed is white (RHS 155C); surface texture of the rhizome is smooth.

Foliage:

*Type*.—Evergreen.

*Abundance*.—Very dense.

*Shape*.—Linear; grass-like.

*Division*.—Simple.

*Arrangement*.—Whorled around an indistinguishable culm.

*Attitude*.—Proximal two-thirds portion of the leaf is semi-erect; distal one-third portion of the leaf is drooping.

*Apex*.—Tridentate. The leaf apex may become locally necrotic in response to moisture stress.

*Base*.—Sheathed attachment to the culm.

*Basal sheath*.—Greyed-orange, RHS 175A; margins tattered; apex is acute.

*Margins*.—Entire.

*Mature leaf dimensions*.—1.8 mm wide and 400 mm long, on average. The leaf is generally a uniform width, narrowing only slightly from base to apex.

*Juvenile foliage color, adaxial & abaxial surfaces*.—146A.

*Mature foliage color, adaxial & abaxial surfaces*.—146A.

*Venation*.—Parallel.

*Vein color, adaxial surfaces*.—Indistinguishable from surrounding foliage.

*Vein color, abaxial surfaces*.—Indistinguishable from surrounding foliage.

*Texture, adaxial surface*.—Glabrous; smooth with light glaucosity.

*Texture, abaxial surface*.—Glabrous; smooth.

Inflorescence:

*Type*.—Racemes containing small clusters of male flowers; some flowers are sessile to the rachis while others are borne on pedicels of varying length.

*Natural flowering season*.—Heavy blooming in spring; sporadic in summer and fall.

*Position*.—Racemes positioned at or slightly above the foliar plane.

*Overall dimensions*.—Up to 260 mm long, including the peduncle and rachis.

*Quantity*.—Very floriferous; inflorescences may potentially arise from every shoot.

*Peduncle*.—Dimensions — Up to 160 mm long and 2 mm in diameter. Attitude — Semi erect to drooping. Strength — Strong. Texture — Smooth. Color — 144B.

*Pedicels*.—Dimensions — Up to 10 mm long and 1.25 mm in diameter. Strength — Strong. Texture — Smooth. Color — 145A.

Bud:

*Dimensions*.—Approximately 2 mm long and 2 mm wide.

*Bud shape*.—Rounded.

*Bud color*.—10B.

*Rate of bud opening*.—Slow.

Flower:

*Shape*.—Cupuliform; cup-shaped.

*Persistence*.—Non-persistent.

*Aspect*.—Erect.

*Fragrance*.—Non-fragrant.

*Perianth*.—Calyx — Shape — Ovate. Dimensions — Approximately 1 mm. Color — 10B. Texture — Smooth. Sepals — Arrangement — Alternate. Quantity — Three. Margin — Entire. Apex — Aristate. Base — Obtuse. Texture — Smooth. Sepal color, immature, upper surface — 165D. Sepal color, immature, under surface — 165D. Sepal color, mature, upper surface — 165D. Sepal color, mature, under surface — 165D. Corolla — Arrangement — Alternate; petals unfused. Dimensions — Approximately 2 mm in diameter and 4 mm deep. Petals — Quantity — Three. Arrangement — Alternate. Dimensions — Approximately 1.5 mm long and 1.0 mm wide. Shape — Ovate. Margin — Entire. Apex — Acute. Base — Obtuse. Texture — Smooth. Color when opening, upper side — Nearest to 150D. Color when opening, under side — Nearest to 150D. Color when fully opened, upper side — 10B. Color when fully opened, under side — 10B. Bracts —

Shape — Needle-shaped. Length — range in length from 6 to 9 mm. Apex — Acute. Margin — Entire. Color — 160D.

Reproduction organs: Not observed.

Seed: Flowers are male; seed is not produced.

COMPARISONS WITH THE PARENT PLANTS

Plants of the new cultivar 'LM600' may be distinguished from its seed parent, a fine-leafed female *Lomandra* Labill. breeding line, by the following combination of characteristics:

1. 'LM600' exhibits a shorter plant height when compared to the seed parent.
2. 'LM600' exhibits a weeping growth habit, whereas the seed parent exhibits an arching growth habit.
3. 'LM600' exhibits dark green foliage, whereas the seed parent exhibits blue-green foliage.
4. 'LM600' exhibits foliage of finer texture when compared to that of the seed parent.

COMPARISONS WITH THE MOST SIMILAR VARIETY OF COMMON KNOWLEDGE

Plants of the new cultivar 'LM600' may be distinguished from the commercial variety, *Lomandra* sp. 'Lime Divine' (not patented), by the following combination of characteristics:

1. 'LM600' exhibits dark green foliage, whereas 'Lime Divine' exhibits light yellow-green foliage.
2. 'LM600' exhibits a short plant height of approximately 25 cm, whereas 'Lime Divine' exhibits at plant height of approximately 50 cm.

Plants of the new cultivar 'LM600' may be distinguished from the commercial variety, *Lomandra* sp. 'Frosty Top' (not patented), by the following combination of characteristics:

1. 'LM600' exhibits dark green foliage, whereas 'Frosty Top' exhibits greyed-green foliage.
2. 'LM600' exhibits a short plant height of approximately 25 cm, whereas 'Frosty Top' exhibits at plant height of approximately 50 cm.

Plants of the new cultivar 'LM600' may be distinguished from the commercial variety, *Lomandra* sp. 'Fine n Dandy' (not patented), in that 'LM600' exhibits a short plant height of approximately 25 cm, whereas 'Fine n Dandy' grows to approximately 80 to 120 cm.

Plants of the new cultivar 'LM600' may be distinguished from the commercial variety, *Lomandra longifolia* 'LM300' (U.S. Plant Pat. No. 15,420), by the following combination of traits:

1. 'LM600' exhibits dark green foliage, whereas 'LM300' exhibits lighter green foliage.
2. 'LM600' exhibits a short plant height of approximately 25 cm, whereas 'LM300' exhibits at plant height of approximately 80 cm.
3. 'LM600' exhibits a finer leaf texture than 'LM300'.

That which is claimed is:

1. A new and distinct variety of *Lomandra* Labill. named 'LM600', substantially as described and illustrated herein.

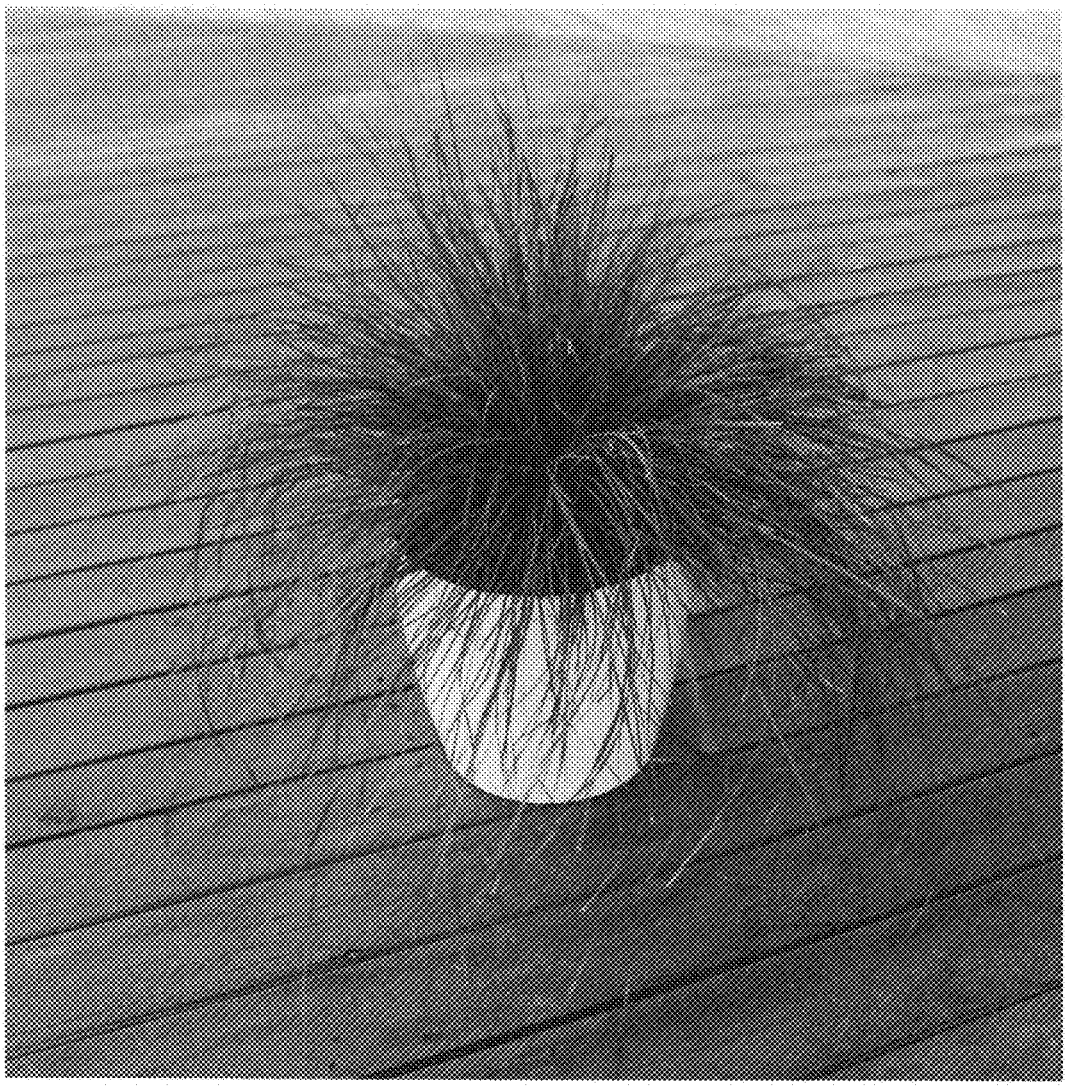

* * * * *